United States Patent
Aebi et al.

[11] Patent Number: 5,326,978
[45] Date of Patent: Jul. 5, 1994

[54] FOCUSED ELECTRON-BOMBARDED DETECTOR

[75] Inventors: Verle Aebi, Menlo Park; Ross A. LaRue, Milpitas; Kenneth Costello, Union City; Stephen J. Bartz, Foster City, all of Calif.

[73] Assignee: Intevac, Inc., Santa Clara, Calif.

[21] Appl. No.: 992,430

[22] Filed: Dec. 17, 1992

[51] Int. Cl.5 .............................. H01J 37/252
[52] U.S. Cl. ................................ 250/397; 250/299
[58] Field of Search ............... 250/397, 299, 214 VT; 313/103 R, 103 CM, 105 R, 105 CM

[56] References Cited

U.S. PATENT DOCUMENTS

| | | | |
|---|---|---|---|
| 3,798,453 | 3/1974 | McIlwain et al. | 250/214 VT |
| 4,785,172 | 11/1988 | Kubena et al. | 250/309 |
| 4,794,296 | 12/1988 | Warde et al. | 313/103 CM |
| 4,814,599 | 3/1989 | Wang | 313/103 CM |
| 4,825,118 | 4/1989 | Kyushima | 313/105 CM |
| 4,918,358 | 4/1990 | Arihara et al. | 250/427 |
| 5,101,100 | 3/1992 | Kinoshita et al. | 250/214 VT |

Primary Examiner—Paul M. Dzierzynski
Assistant Examiner—Kiet T. Nguyen
Attorney, Agent, or Firm—Stanley Z. Cole

[57] ABSTRACT

A focused electron-bombarded (FEB) ion detector comprising an MCP, focusing means, and a collection anode disposed in a detector body. The collection anode includes a diode for receiving the focused output electron beam from the MCP. The gain between the input ion current to the MCP and the detector output signal from the diode is on the order of 1–100 million, depending on the device configuration and applied biasing voltages.

18 Claims, 3 Drawing Sheets

FOCUSED ELECTRON-BOMBARDED DETECTOR

BACKGROUND OF THE INVENTION

This invention relates to focused, electron-bombarded (FEB) detectors, particularly to FEB ion detectors.

Ion detectors are used to measure charged particle flux or current in a vacuum. When used in mass spectrometers, for example, ion detectors measure the flux of charged particles moving through an orthogonal magnetic field of a predetermined magnitude and bending according to their charge to mass ratios. Other applications include scanning electron microscopy; UV and X-ray spectroscopy; E-beam/X-ray lithography; field ion microscopy; and charged particle/photon imaging. Prior art mass spectrometers and other devices use channeltrons or stacks of microchannel plates (MCPs) as ion detectors.

A channeltron or channel multiplier is based on the continuous dynode electron multiplier concept first suggested by P. T. Farnsworth in U.S. Pat. No. 1,969,399. The channel multiplier consists of a hollow tube coated on the interior surface by a secondary electron emitting semiconductor layer. This layer emits secondary electrons in response to bombardment by electromagnetic radiation or particles such as electrons. Input and output electrodes are provided on each end of the tube to create a bias voltage which accelerates the emitted secondary electrons down the channel. Secondary electrons also strike the wall, releasing additional secondary electrons. The resulting amplification of the input photon or particle is called the device's gain.

MCPs operate on the same basic principles as channeltrons. A typical MCP is comprised of a million parallel channels 4-20 microns in diameter and 40-500 microns long. The channels are typically formed at a small angle of a few degrees relative to the normal MCP surface to ensure that ions generated at the tube anode cannot be accelerated down the channel but instead strike the channel wall near the back of the MCP. MCPs may be stacked to multiply the effect of their gains. When stacked, the channel angles of alternating plates are reversed, giving rise to the designation "Chevron" or "Z" stack.

One drawback of prior art ion detectors such as channeltrons and MCP stacks is their relatively large capacitance, which limits their bandwidth and response time. Another drawback of prior art ion detectors is their limited dynamic range. This second drawback is due, in part, to the high gains needed for certain applications. At high bias voltages, channeltrons and MCP stacks can become nonlinear in their output current responses to input currents.

Yet another drawback of current detectors is the need to operate the MCP stack or channeltron at high bias voltages. High bias voltages accelerate the degradation of the electron-emitting channel surfaces. In addition, operation of the devices under high biases requires the maintenance of a high vacuum to minimize the effect of ion feedback on the performance of the devices.

What is needed, therefore, is an ion detector that has increased dynamic range, bandwidth and shorter response time.

SUMMARY OF THE INVENTION

This invention meets this and other needs by providing an improved FEB detector. In the preferred embodiment, the invention is a focused electron-bombarded (FEB) ion detector comprising an MCP, a pair of focusing rings, and a collection anode disposed in a detector body. The collection anode includes a diode for receiving the focused output electron beam that issues from the MCP. The gain between the input ion current to the MCP and the detector output signal from the diode is on the order of 10-100 million, depending on the device configuration and applied biasing voltages.

The invention is described in more detail below with reference to the drawings.

DETAILED DESCRIPTION OF THE PREFERRED EMBODIMENT

Figure 1:
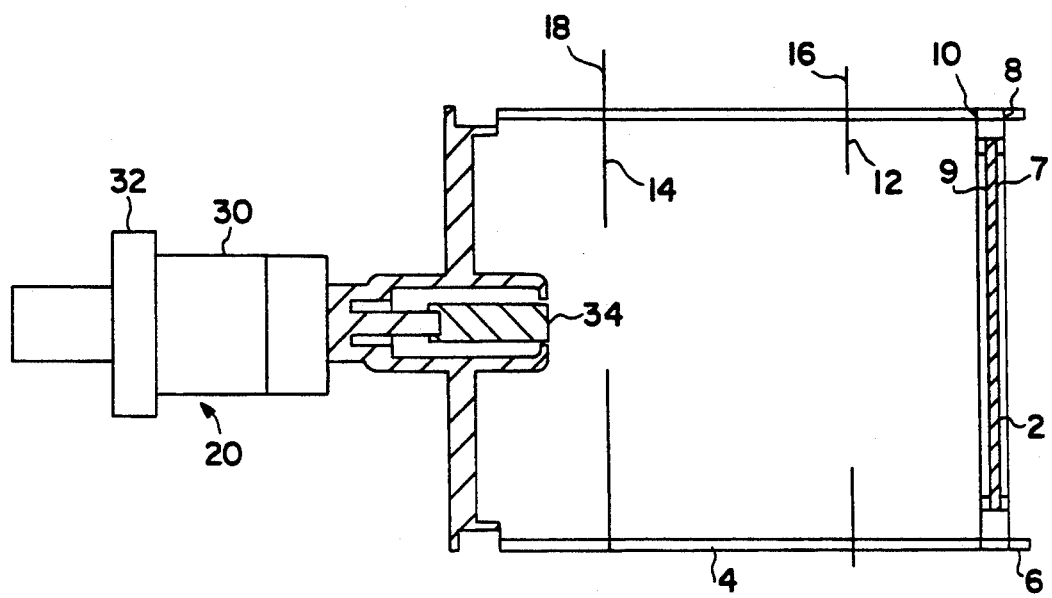
FIG. 1 is a cross-sectional view of an FEB ion detector according to the preferred embodiment of this invention.
Figure 2:
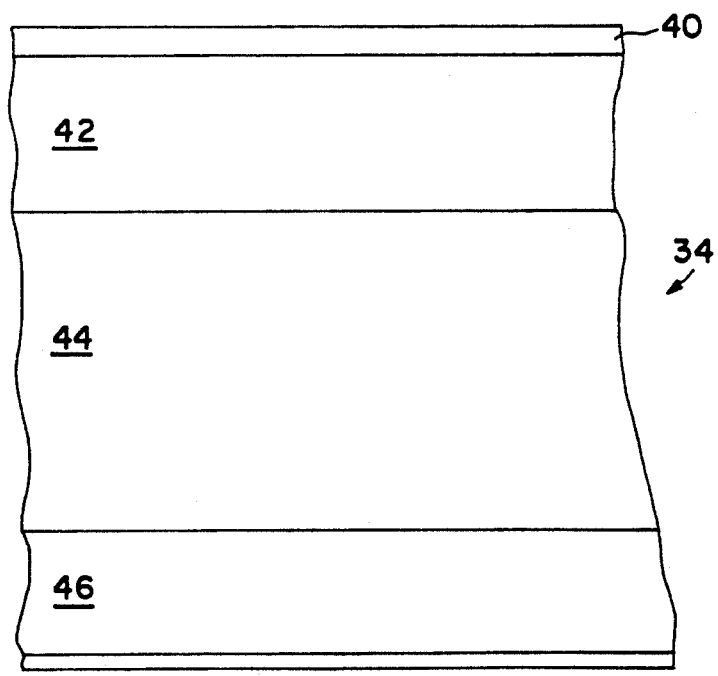
FIG. 2 is a detailed view of the diode element of the preferred embodiment.

The preferred embodiment of the invention is an FEB ion detector as shown in FIGS. 1 and 2. A standard microchannel plate (MCP) 2 is mounted at one end of a cylindrical detector body 4. In the embodiment shown in FIG. 1, detector body 4 is comprised of a series of ceramic rings stacked to give the appropriate dimensions. Alternatively, the detector body could be formed as a specially designed cylinder or in any other shape dictated by the application. MCP 2 is held in place by a retainer ring 6. Conductors 8 and 10 extend from the MCP input electrode 7 and MCP output electrode 9, respectively, to attach the ion detector to a suitable power source (not shown).

Figure 3:
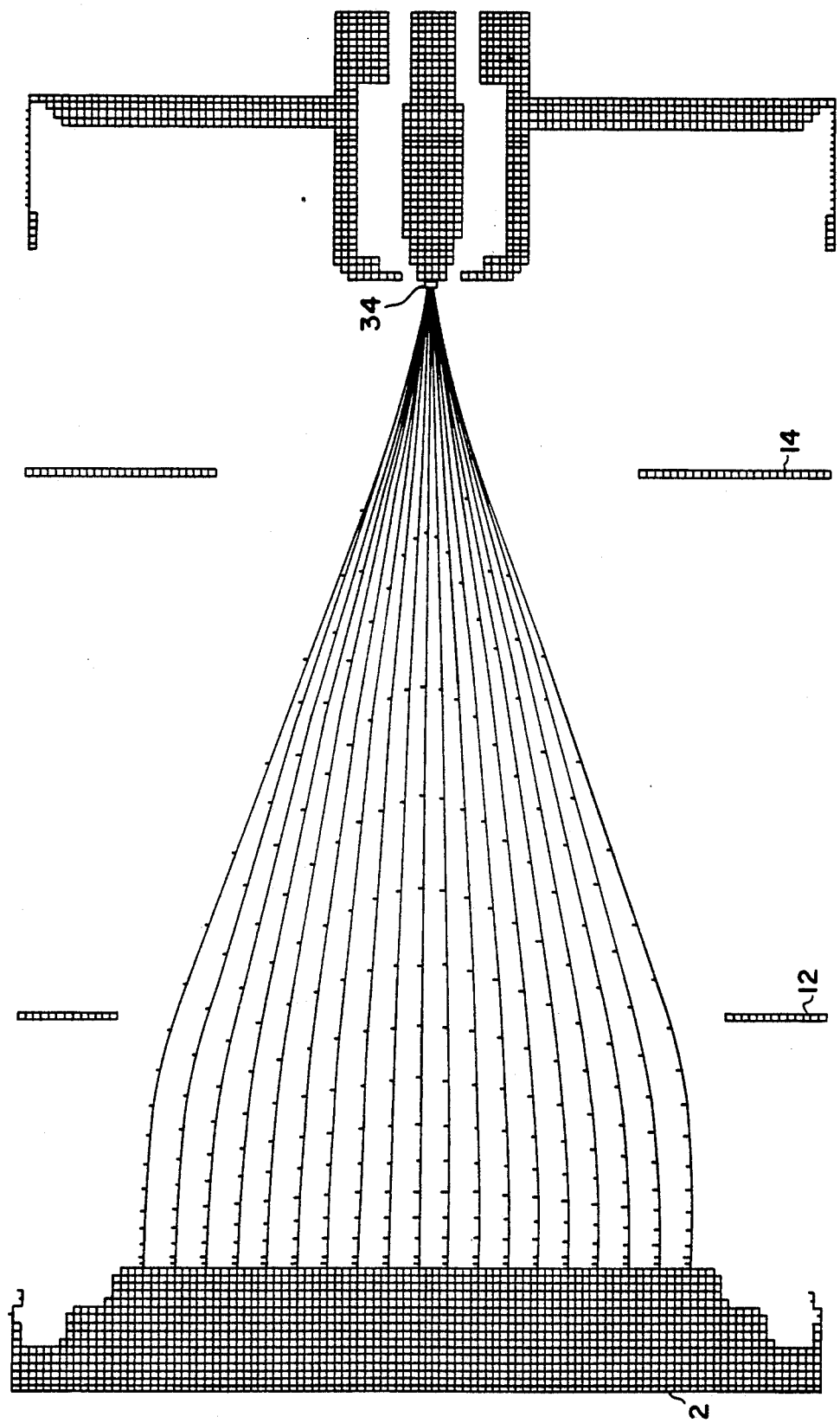
FIG. 3 is a schematic drawing showing the operation of the FEB ion detector of the preferred embodiment.

Two electron focusing rings 12 and 14 are disposed in detector body 4. In the embodiment shown in FIG. 1, rings 12 and 14 are mounted between pairs of the ceramic rings comprising detector body 4. Other means of attaching the focusing rings may be used without departing from the invention. Rings 12 and 14 connect to an external power source (not shown) via suitable conductors 16 and 18, respectively. The purpose of focusing rings 12 and 14 is to concentrate and direct the output of the MCP onto the collection anode, as shown schematically in FIG. 3. An alternative approach is to use known electromagnetic focusing means (not shown) as is well known. A collection anode 20 is disposed at the far end of detector body 4. Anode 20 comprises a broadband microwave connector 30, a step-tapered coaxial transmission line section 32, and a solid state diode 34 terminating the transmission line. In the preferred embodiment, diode 34 is an AlGaAs/GaAs pin diode optimized for electron bombardment current gain. As shown in more detail in FIG. 2, the preferred embodiment of diode 34 comprises three separate layers 40, 42, and 44 formed on a n+ GaAs substrate 46. The top layer 40 is doped to be a p-type $Al_{30}Ga_{70}As$ layer approximately 250 Å thick. Layer 40 provides a potential barrier near the surface of the diode to keep generated electron minority carriers from recombining at the surface. The composition of layer 40 is also chosen for stability and for its resistance to oxidation during processing in air. Layer 42 is doped to be p-type GaAs approximately 0.25 microns thick.

Layer 44 is undoped GaAs and is approximately 6 microns thick. The thickness of layer 44 is chosen to optimize the response time of the diode according to the following principles:

The transit time $T_{transit}$ of an electron across an undoped layer of thickness w is $$T_{transit} = \frac{w}{V_{sat}}$$

where $V_{sat}$ is $1 \times 10^7$ $cm/sec$. The RC time constant $T_{RC}$ of the loaded diode is $$T_{RC} = E \frac{\pi r^2}{w} R_L$$

where r is the radius of the diode and $R_L$ is the diode load (50Ω, for example). The time response of the loaded diode is minimized when $T_{transit} = T_{RC}$ or, $$\frac{w}{V_{sat}} = E \frac{\pi r^2}{w} R_L$$

The optimum w or undoped thickness is therefore w = Square Root of ($E\pi$ $r^2$ $V_{sat}R_L$).

The optimum time response is therefore $T_{opt}$ = Square Root of ($E\pi$ $r^2$ $R_L/V_{sat}$).

Since $T_{opt}$ is proportional to diode radius, the time response of an FEB detector using such a diode is greatly improved over detectors which do not focus.

The following is an example of the design and operating parameters of an FEB ion detector according to a preferred embodiment of the invention. The MCP of this example has a plate diameter of 18 mm and a channel diameter of 10 microns. An outside power source applies a potential of approximately 1000 volts across the MCP's input and output electrodes 7 and 9. In addition, the power source applies a potential of approximately 30 volts between MCP output electrode 9 and the first focusing ring 12 and a potential of approximately 400 volts between MCP output electrode 9 and the second focusing ring 14. Collection anode 20 is grounded, making the voltage drop between diode 34 and the MCP output approximately 10,000 volts.

Figure 4A:
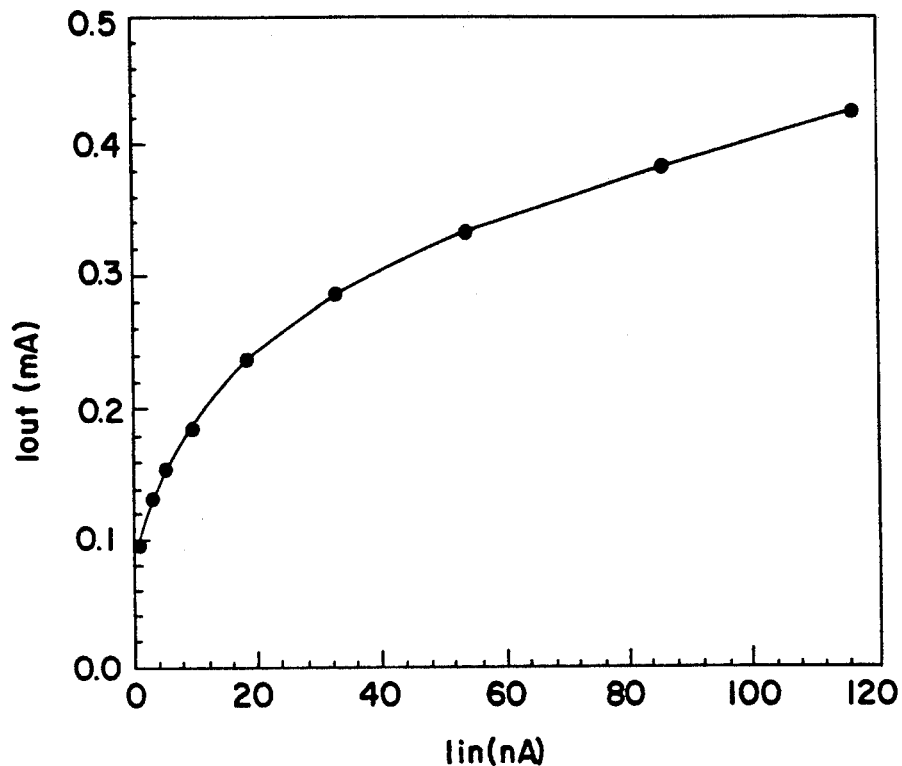
FIG. 4A is an actual measured transfer curve of output current vs. input current
Figure 4B:
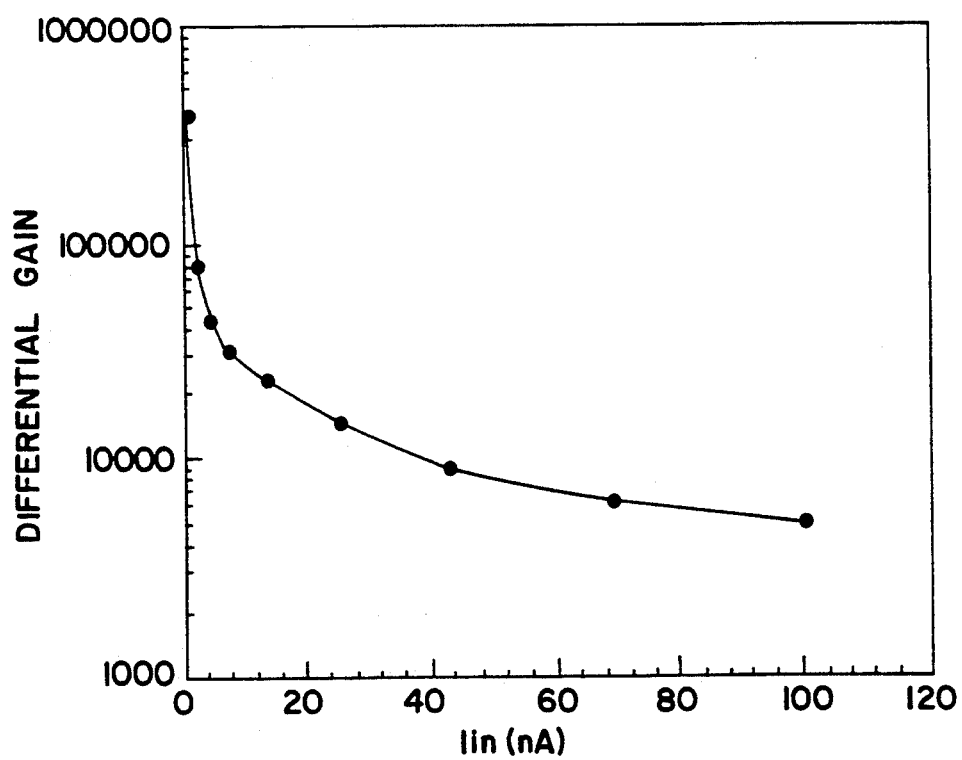
FIG. 4B is a curve illustrating the differential gain vs. input current calculated from FIG. 4A.

In operation, charged particles (such as positive ions) strike the MCP channel walls and create electrons. The electrons are accelerated by the voltage across the MCP and strike the channel walls to generate additional electrons. This multiplication of electrons results in a flux of electrons at the MCP output end with a net gain of electron charge per incident charged particle. The generated electrons are then accelerated and focused by the focusing rings 12 and 14. The focusing rings of the FEB ion detector reduce the diameter of the MCP output from 18 mm at the output electrode to a 0.25 mm diameter beam at collection anode 20 (as shown schematically in FIG. 3), and the bias applied to the MCP and focusing rings raises the average energy of the electrons striking diode 34 to 10,000 eV. The gain of the FEB ion detector may be adjusted by changing the bias voltage of the MCP (i.e., by changing the voltage between the MCP input and output electrodes) and by changing the overall bias between the MCP, the focusing rings and the collection anode. For an MCP bias voltage of 1000 volts and overall bias voltage of 10,000 volts as described in this example, the FEB ion detector gain is on the order of 90 million. FIG. 4A shows the measured transfer curve (diode output current versus input current) and 4B shows the differential gain of a prototype FEB ion detector. Here the detector is used to detect input electron current. The gain is approaching one million at one nanoamp input current.

The FEB detector of this invention improves upon current ion detectors such as channeltrons and MCP stacks by improving the device's bandwidth and dynamic range due to the pin diode's ability to handle relatively high instantaneous currents while still delivering a linear response. The FEB detector also has a lower capacitance, and therefore a faster recovery time, than prior art detectors.

The FEB detector of this invention has a longer useful life than current channeltron or MCP stack ion detectors. The high gain at which channeltrons and MCP stacks need to be operated increases the electron bombardment rate on the devices' outputs. The higher bombardment rate deteriorates the interior surface of the channels, causing them to be less emissive. However, this form of deterioration is avoided with the FEB ion detector of this invention because the MCP is operated at a lower gain.

The FEB detector of this invention does not have the same stringent vacuum requirements that MCP stacks and channeltrons have. The high gain of current MCP stacks and channeltrons creates high electron densities within the channels. Collisions between the electrons and any gas molecules present in the channels can create positive ions. As the positive ions move toward the input end of the channels under the influence of the bias voltage, they strike the channel walls and create "noise" electrons. Higher bias voltages create more ions and increase this noise effect. Since the FEB detector of this invention can be operated at lower bias voltages than current channeltrons and MCP stacks, fewer ions are created in the channels at given gas molecule concentrations. The FEB detector of this invention can therefore be used under less stringent vacuum conditions than current detectors with ion noise effect kept to a minimum.

The example described above is but one of many possible configurations; other configurations of FEB detectors are within the scope of this invention. In one alternative embodiment, for example, a silicon or GaAs avalanche photodiode may be substituted for the solid state diode described above to give added gain. In addition, the detector could employ more than one MCP in a serial (stacked) arrangement to improve the gain of the detector.

In another alternative embodiment, the focusing rings may be modified and more focusing rings may be added to optimize the focusing for the application. In addition, the single diode 34 may be replace with an array of diodes to provide positional information.

The dimensions and properties of the FEB detector should be selected to meet the application. For example, the MCP may be designed with a larger diameter to increase the detector input area. The communication between the diode and the device monitor may be optimized by impedance matching the diode and the coaxial transmission line in a manner known in the art. Impedance matching helps keep the response of the detector flat over the dynamic range of frequencies.

While this invention has been described with reference to the detection of ions, the invention may be used to detect any particle that generates electrons when striking the channel walls of an MCP, such as an X-ray, a photon or an energetic neutral particle. In addition, although this invention has been described in terms of ordinary MCPs, the walls of such MCPs may also be doped or coated to enhance the electron generation effect in a manner known in the art, for use in this invention.

Other modifications will be apparent to those skilled in the art.

We claim:

1. A charged particle detector comprising:
   a microchannel plate for generating electrons in response to the impact of a charged particle on a surface of the microchannel plate;
   acceleration means for accelerating the electrons generated by the microchannel plate;
   focusing means for focusing the accelerated electrons in a predetermined direction along an electron beam path; and
   transducer means comprising a solid state diode for detecting the electrons focused by the focusing means and for generating a signal representative of energy of the charged particle.

2. The charged particle detector of claim 1 wherein the acceleration means comprises an electrode.

3. The charged particle detector of claim 1 wherein the focusing means comprises a first focusing ring surrounding the electron beam path.

4. The charged particle detector of claim 3 wherein the focusing means further comprises a second focusing ring surrounding the electron beam path.

5. The charged particle detector of claim 1 wherein the transducer means comprises an array of diodes.

6. The charged particle detector of claim 1 wherein the focusing means is electromagnetic.

7. A charged particle detector comprising:
   microchannel plate means for generating electrons in response to the impact of charged particles on a surface of the microchannel plate means;
   accelerator means for accelerating the electrons generated by the microchannel plate;
   focusing means for focusing the electrons generated by the microchannel plate in a predetermined direction along an electron beam path, the focusing means comprising a focusing ring surrounding the electron beam path; and
   a diode for detecting the electrons focused by the focusing means and for generating a signal representative of energy of the charged particles.

8. The charged particle detector of claim 7 wherein the diode comprises an avalanche photodiode.

9. The charged particle detector of claim 7 wherein the diode comprises a solid state diode.

10. The charged particle detector of claim 9 wherein the focusing means further comprises a second focusing ring surrounding the electron beam path.

11. The charged particle detector of claim 9 wherein the microchannel plate means comprises a plurality of microchannel plates arranged in series.

12. A method of a charged particle detector for measuring a flux of a charged particle input moving along a current path comprising the following steps of:
   placing a microchannel plate in the current path;
   applying a bias voltage to the microchannel plate to generate an electron beam output from the charged particle input impacted on a surface of the microchannel plate;
   accelerating the electron beam output;
   focusing the accelerated electron beam output onto a detecting diode; and
   generating an energy signal proportional to the flux of the charged particle input.

13. A charged particle detector in which a collection area is at least a hundred times greater than an output area of a transducer at an output end of the detector comprising:
   a collection transducer comprising at least a microchannel plate to generate electrons in response to the impact of a charged particle on a surface of the microchannel plate;
   accelerator means for accelerating the electrons generated by said microchannel plate;
   focusing means for focusing said accelerated electrons along a predetermined electron beam path; and
   transducer means comprising a diode for detecting the focused electrons and for generating a signal representative of energy of the charged particle.

14. The charged particle detector of claim 13 wherein the diode comprises a solid state diode.

15. The charged particle detector of claim 13 wherein the diode comprises an avalanche photodiode.

16. The charged particle detector of claim 13 wherein the focusing means comprises focusing rings surrounding the electron path.

17. The charged particle detector of claim 13 wherein the microchannel plate has a diameter of at least 18 mm. and the electrons are focused to about 0.25 mm diameter at said transducer diode.

18. The charged particle detector of claim 13 wherein said collection transducer is a plurality of microchannel plates in a cooperating relationship.

* * * * *